United States Patent [19]

Parker

[11] Patent Number: 5,700,253
[45] Date of Patent: Dec. 23, 1997

[54] FLEXIBLE, KINK-RESISTANT, INTRODUCER SHEATH AND METHOD OF MANUFACTURE

[75] Inventor: Fred T. Parker, Bloomington, Ind.

[73] Assignee: Cook Incorporated, Bloomington, Ind.

[21] Appl. No.: 370,926

[22] Filed: Jan. 10, 1995

Related U.S. Application Data

[60] Division of Ser. No. 21,398, Feb. 23, 1993, Pat. No. 5,380,304, and a continuation-in-part of Ser. No. 741,689, Aug. 7, 1991, abandoned.

[51] Int. Cl.[6] ................................................. A61M 25/00
[52] U.S. Cl. ................................... 604/282; 604/280
[58] Field of Search ............................ 604/280, 282, 604/204; 128/656, 657, 658

[56] References Cited

U.S. PATENT DOCUMENTS

| | | | |
|---|---|---|---|
| 3,485,234 | 12/1969 | Stevens | 604/282 X |
| 3,498,286 | 3/1970 | Polyani et al. | 604/282 X |
| 3,924,632 | 12/1975 | Cook | 604/282 |
| 4,044,765 | 8/1977 | Kline | 604/282 X |
| 4,425,919 | 1/1984 | Alson, Jr. et al. | 604/282 X |
| 5,217,440 | 6/1993 | Frassica | 604/282 |

Primary Examiner—Sam Rimell
Attorney, Agent, or Firm—Richard J. Godlewski

[57] ABSTRACT

A flexible, kink-resistant, introducer sheath for percutaneous vascular access. The introducer sheath includes a flat wire coil with uniform spacing between the turns, which is compression fitted about an inner, lubricous material polytetrafluoroethylene tube. The introducer sheath further includes an outer tube of a heat formable polyamide material which is heat formed and compressed through the spaces between the turns of the wire coil to mechanically connect to the roughened outer surface of the inner tube. The distal end of the outer tube is tapered in a mold with additional polyamide outer tube material. The proximal end of the sheath is flared for connection to a connector fitting. In another aspect of the introducer sheath, the flat wire coil has an inner diameter less than the outer diameter of the inner tube. The coil is then expanded and wrapped around the inner tube to form a compression fit.

20 Claims, 4 Drawing Sheets

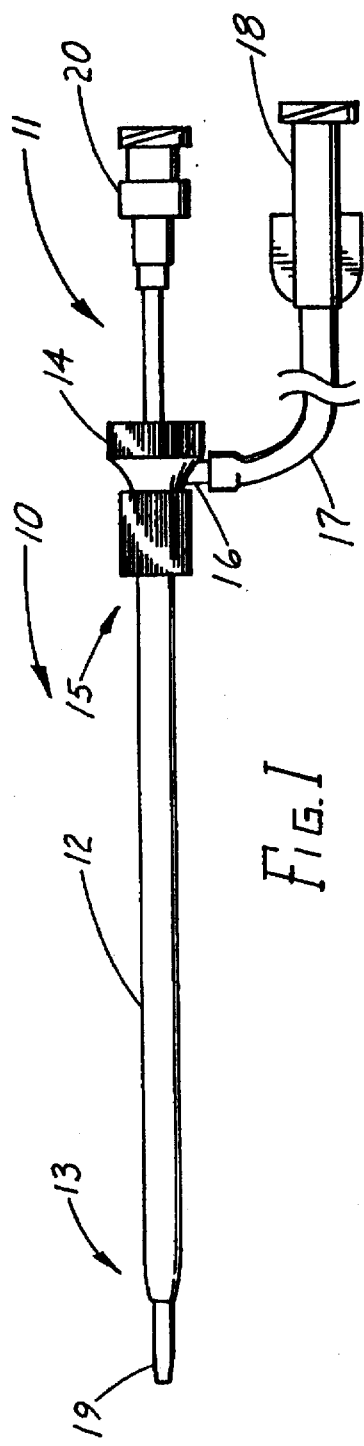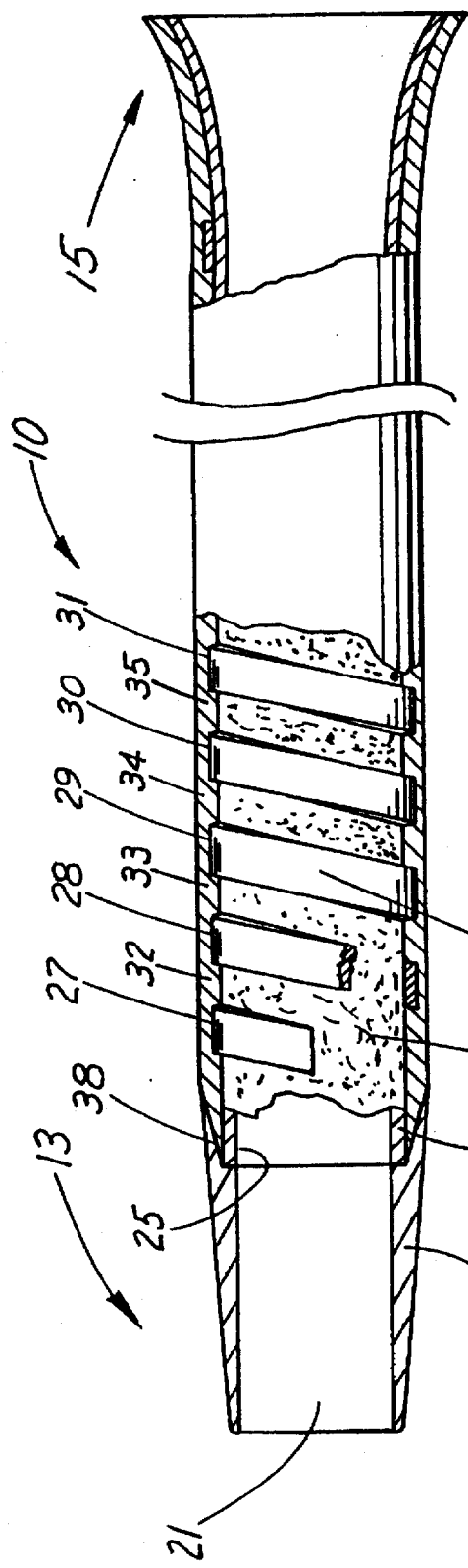

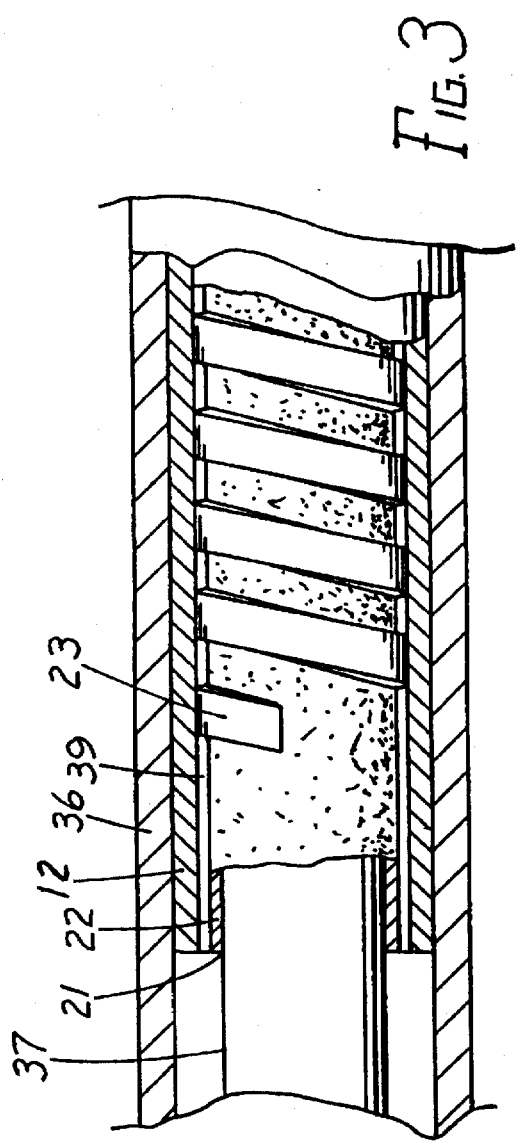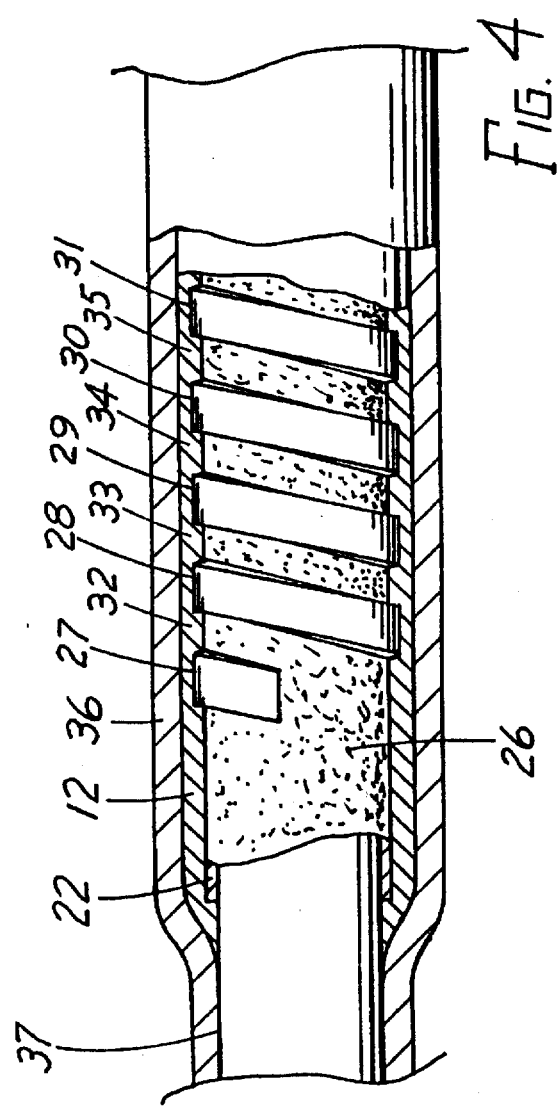

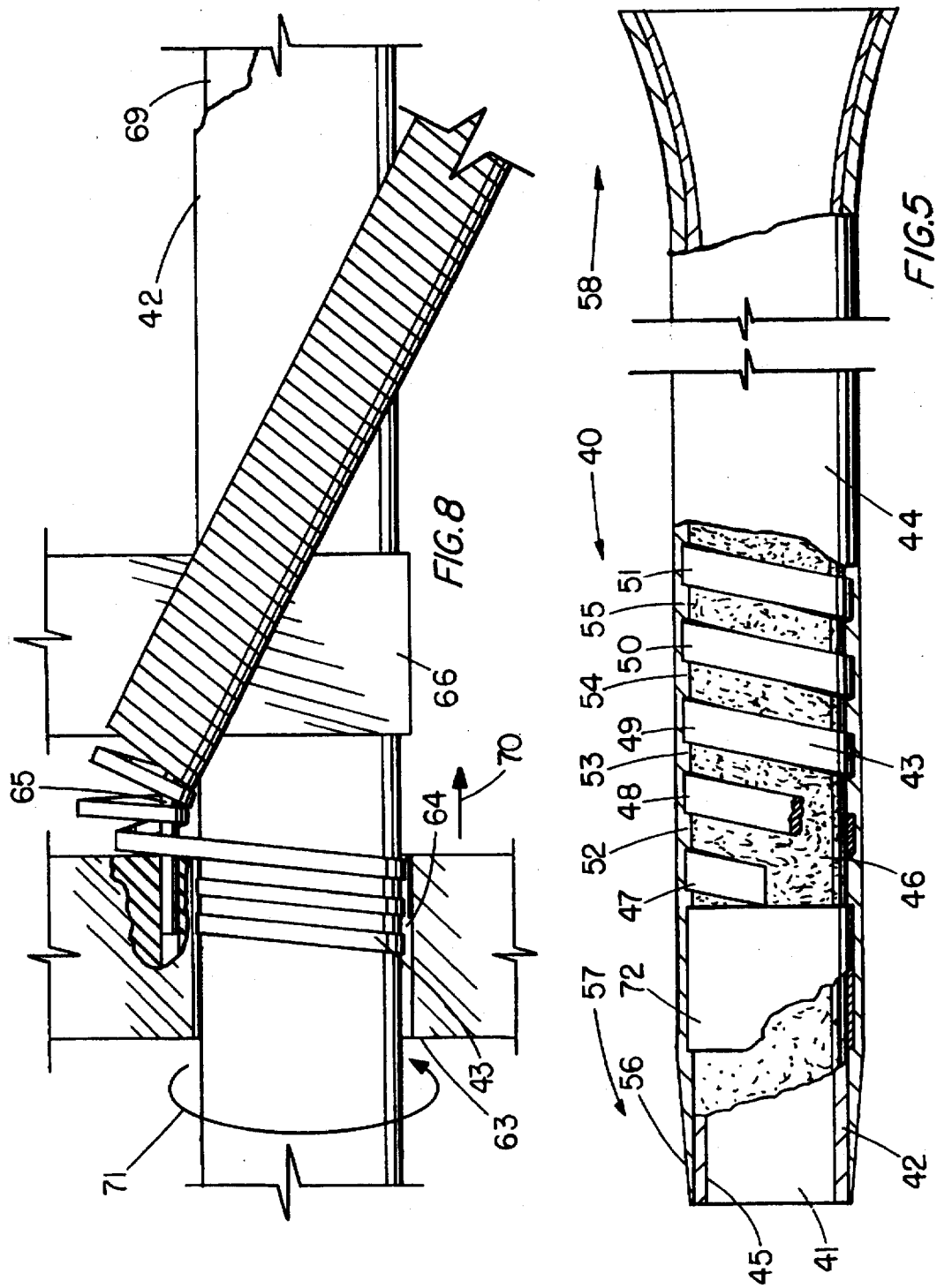

FLEXIBLE, KINK-RESISTANT, INTRODUCER SHEATH AND METHOD OF MANUFACTURE

CROSS-REFERENCE TO RELATED APPLICATIONS

This application is a division of application Ser. No. 08/021,398 for a Flexible, Kink-Resistant Introducer Sheath, filed Feb. 23, 1993, and issuing Jan. 10, 1995, as U.S. Pat. No. 5,380,304, and a continuation-in-part of application Ser. No. 07/741,689 for a Flexible, Kink-Resistant Introducer Sheath, filed Aug. 7, 1991, now abandoned.

TECHNICAL FIELD

This invention relates generally to sheaths for maintaining vascular access and for introducing catheters and medication therethrough and, in particular, to a flexible, kink-resistant, introducer sheath.

BACKGROUND OF THE INVENTION

Introducer sheaths are well-known for percutaneous vascular access and typically comprise polytetrafluoroethylene or fluorinated ethylene propylene. These sheaths are of a thin-wall construction, but tend to kink. Increasing the thickness of the sheath wall minimally improves the level of kink resistance, which is still unacceptable. Sheaths used in hemofiltration and dialysis, in particular, are prone to kinking since they remain positioned in a patient's body for a long time. While positioned in a patient, the sheath may be bent or pinched off and, as a result, kink due to repeated use or patient movement. A kinked sheath is unusable and cannot be straightened while positioned in the body of a patient. Consequently, the sheath must be removed, leaving an enlarged, bleeding opening, which typically cannot be reused. Vascular access is then attempted at an alternative site, and the procedure is restarted. Restarting the procedure causes a time delay, which may be life threatening. In some cases, an alternative site is not available for introducing another sheath.

Another problem with thin-wall sheaths is that an emergency room physician will typically kink an introducer sheath while inserting various catheters therethrough during emergency procedures. Small diameter introducer sheaths are also typically bent and kinked under the time constraints of an emergency situation. As a result, a new sheath must be introduced at the same or another access site.

Another introducer sheath is described in U.S. Pat. Nos. 4,634,432; 4,657,772; and 4,705,511. This introducer sheath utilizes a helical coil spring and a cylindrical wall formed by dipping the spring in a protective coating composition, which completely surrounds the spring. The coating composition comprises a thermoplastic polymer material dissolved in a solvent solution. Although this introducer sheath appears to be more kink-resistant and flexible than a polytetrafluoroethylene sheath, the cylindrical wall is approximately twice as thick as that of the polytetrafluoroethylene sheath with the same inside diameter. The increased outside diameter of this introducer sheath significantly increases the size of the access site, which further accentuates the problem of bleeding.

SUMMARY OF THE INVENTION

The foregoing problems are solved and a technical advance is achieved in an illustrative flexible, kink-resistant, introducer sheath comprising a coil having a plurality of turns positioned and compression fitted around an inner tube. An outer tube is connected to the inner tube through the uniform spacing of the coil turns. As a result, the compression fitted coil reinforces the wall to provide an extremely kink-resistant and thin-walled introducer sheath. A predetermined uniform spacing between the coils is also utilized since extremely wide spacing weakens the wall and creates a rough surface. Narrow spacing does not allow sufficient room for connecting the outer tube to the inner tube. In the preferred embodiment, the coil comprises a flat wire coil for further improving the strength of the introducer sheath.

The wall of the inner tube advantageously prevents the coil turns from extending into the inner tube passageway. As a result, the inner tube passageway has a uniform diameter for passing the largest possible diameter catheter therethrough. In contrast, the protrusion of coil turns into the passageway establishes a varying diameter, which limits the size of the catheter passable therethrough. The inner tube also comprises a lubricous material such as polytetrafluoroethylene, which presents a slippery surface for easy insertion of a catheter therethrough. Furthermore, the inner tube includes a smooth inner surface for resisting the formation of blood clots thereon. The inner tube also advantageously includes a rough outer surface for improving the connection of the outer tube thereto through the uniform spacing of the coil turns.

The outer tube advantageously comprises a heat formable polyamide material such as nylon for mechanically connecting with the rough outer surface of the inner tube. The sheath further comprises a heat shrinkable tube positioned around the outer tube for compressing the outer tube between the uniform spacing of the compression-fitted coil turns and mechanically connecting the outer tube to the rough surface of the inner tube when heated. The heat formable polyamide material is also advantageously self-leveling for providing a smooth outer surface which also reduces the formation of blood clots thereon.

The distal ends of the inner and outer tubes extend beyond the distal end of the coil. The distal end of the outer tube is tapered and extends beyond the distal end of the inner tube to advantageously prevent the inner tube from presenting a rough edge or surface, which may cause injury to the vessel wall. The inner diameter of the passageway about the distal ends of the inner and outer tubes is uniform to again minimize the formation of blood clots on the inner surface of the inner tube.

The proximal ends of the inner and outer tubes also extend beyond the proximal end of the coil and are flared for attachment to a connector.

In another aspect of the present invention, a coil having an inner diameter smaller than the outer diameter of the inner tube is wound around and compression fitted around the inner tube. This advantageously eliminates collapsing the inner tube for insertion into the passage of the flat wire coil. This also advantageously eliminates the formation of any wrinkles in the inner tube when the collapsed inner tube is expanded to form a compression fit against the flat wire coil.

A radiopaque marker is positioned adjacent the distal end of the coil to improve visualization of the sheath when inserted in a patient.

The method of manufacturing a flexible, kink-resistant, introducer sheath includes expanding the flat wire coil with a inner diameter less than the outer diameter of the inner tube and wrapping the coil when expanded around the inner tube. The outer tube is then longitudinally positioned around the inner tube and flat wire coil and connected to the inner tube through spaces between the turns of the coil.

BRIEF DESCRIPTION OF THE DRAWING

FIG. 1 depicts an illustrative flexible, kink-resistant, introducer sheath of the present invention;

FIG. 2 depicts a partially sectioned view of the introducer sheath of FIG. 1;

FIG. 3 depicts a partially sectioned view of the introducer sheath of the present invention with a heat shrink tube prior to being heated;

FIG. 4 depicts a partially sectioned view of the introducer sheath of FIG. 3 with the heat shrink tube heated and the outer tube resultingly formed;

FIG. 5 depicts a partially sectioned view of another aspect of the present invention and an alternative embodiment of the sheath of FIG. 2;

FIG. 8 depicts an enlarged view of a portion of the coil transfer mechanism of FIG. 7.

DETAILED DESCRIPTION

Figure 7:
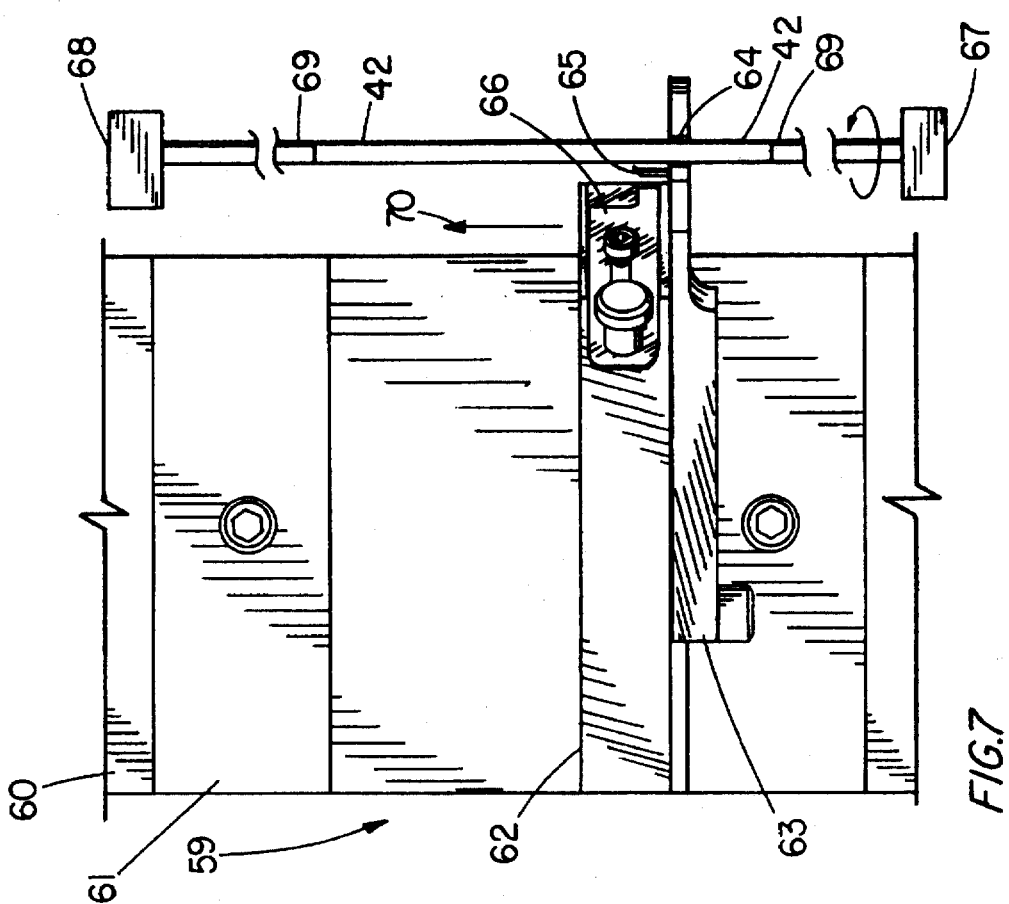
FIG. 7 depicts a top view of the coil transfer mechanism of FIG. 6.

FIG. 1 depicts an illustrative flexible, kink-resistant, introducer sheath 10 with a tapered dilator 11 extending longitudinally through the passageway of the sheath. As shown, the introducer sheath includes an outer tube 12 with a tapered distal end 13 and connector valve 14 attached about proximal end 15 of the sheath. Well-known connector valve 14 includes a silicone disk (not shown) for preventing the backflow of fluids therethrough. The disk includes a slit for the insertion of dilator 11. By way of example, the dilator 11 has a 6.0 French (0.079") outside diameter. Connector 14 also includes side arm 16 to which polyvinyl tube 17 and male Luer lock connector 18 are connected for introducing and aspirating fluids therethrough. Dilator 11 includes tapered distal end 19 for accessing and dilating a vascular access site over a well-known and commercially available wire guide. The guide is inserted in the vessel with an introducer needle using, for example, the well-known percutaneous vascular access Seldinger technique. A well-known male Luer lock connector hub 20 is attached at the proximal end of the dilator for connection to syringes and other medical apparatus.

Depicted in FIG. 2 is a partially sectioned view of introducer sheath 10 with dilator 11 removed from longitudinal passageway 21. The sheath comprises inner tube 22, flat wire coil 23 compression fitted therearound, and outer tube 12 mechanically connected to roughened outer surface 26 of the inner tube through the spacings of the coil. Inner tube 22 is a 7.4 cm length of a lubricous material tube such as polytetrafluoroethylene having a uniform inside diameter in the range of 0.0825" to 0.0840" with a wall thickness of 0.0015" plus or minus 0.0005" before heating. The inner tube has a minimum inside dimension of 0.081" after heating. The lubricous polytetrafluoroethylene material presents a slippery inner surface 25 for the easy insertion and withdrawal of the dilator as well as other catheters and medical apparatus. Inner surface 25 is also smooth and nonporous for minimizing the formation of blood clots and other thrombi thereon. Outer surface 26 of the inner tube is chemically etched in a well-known manner for forming a rough outer surface to which outer tube 12 is mechanically connected using a well-known heat shrinking and formation process. The uniform inner diameter of inner tube 22 extends the entire length of passageway 21 for passing the largest possible diameter catheter therethrough. The wall of the inner tube prevents the turns of compression-fitted coil 23 from protruding into inner tube passageway 21.

Coil 23 comprises a plurality of flat wire turns, for example, 27–31, with uniform spacing including equal width spaces 32–35 therebetween. Coil 23 is 6.5 cm in length with an outside diameter of 0.0942" plus or minus 0.0020" formed from 0.003" thick by 0.012" wide flat rectangular stainless steel wire wound with a uniform space in the range of 0.005" to 0.015" between the turns of the coil. Wire coil 23 is compression fitted around the outer surface of inner tube 22 approximately 4 mm from the distal end thereof and approximately 5 mm from the proximal end thereof to maintain the uniform spacing between the turns of the coil. The coil is compression fitted by collapsing inner tube 22 and inserting the wire coil thereover. Inner tube 22 is then compressed-air expanded to engage and compression fit the inner surface of the flat wire coil. A mandril inserted through the passageway of the inner tube further compresses the inner tube against the coil turns during the manufacture of the sheath as hereinafter described. The coil is positioned away from the distal and proximal ends of the inner tube to permit tapering and flaring of the sheath without extending the coil turns through the polyamide material of the outer tube.

Outer tube 12 is 7.4 cm in length with an inside diameter of 0.103" plus or minus 0.002" of a heat formable polyamide material such as nylon that is heat shrunk over coil 23, which in turn is compression fitted over inner tube 22. The wall thickness of the nylon tube is approximately 0.0065" plus or minus 0.001". The outer tube is heated and compressed through the spaces between the coil turns with a heat shrink tube for mechanically connecting to rough outer surface 26 of the inner tube. As a result, the outside diameter of the outer tube is approximately 0.022" greater than that of the inner tube. After the outer tube is heat shrunk onto the roughened surface of the inner tube, the shrink tube is removed therefrom, and a taper formed at the distal end of the sheath. As a result, the thickness of the sheath including the inner tube, coil, and outer tube is approximately 0.011". The 4 mm length about the distal end of the inner and outer tubes are cut to within a range of 0.010" to 0.090" from the end of coil 23 depending on the inside diameter of the sheath. For a 6.0 French introducer sheath, approximately 0.020" of outer tube 12 is externally tapered about the distal end in a well-known manner to form contact surface area 38. Tapered distal end 13 is formed by cutting and slitting a 3 mm length of nylon tubing having a 0.100" inside diameter and inserting it into a well-known taper mold. The short length of tubing is heated, and the distal end of the sheath with a mandril inserted therethrough is inserted into the taper mold to thermally bond nylon tip material 24 to the outer tube and to form tapered distal end 13, as shown. As a result, the inside diameter of outer tube 12 and inner tube 22 about the distal end thereof assumes the uniform inner diameter of the inner tube. After the distal end is tapered, the outer tube extends approximately 0.120" beyond the distal end of the inner tube and 0.140" beyond the distal end of the flat wire coil. The distal end of inner tube 22 may vary along the length of the tapered distal end of the outer tube, but should not extend all the way to the distal end of the outer tube so as not to break the tapered surface of the outer tube. In this particular embodiment, nylon tip material 24 is of the same durometer as that of outer tube 12. However, it is contemplated that the tip material may have a durometer other than that of the outer tube material. It is further contemplated that the tip material may have a harder durometer so as to further facilitate entry into the access site. Proximal end 15 of the sheath is formed into a flared configuration in a well-known manner such as inserting over a heated, tapered tip end and then cooled.

FIG. 3 depicts a partially sectioned view of introducer sheath 10 with heat shrink tube 36 positioned over outer tube 12 and flat wire coil 23 with longitudinal space 39 therebetween. As previously described, flat wire coil 23 is compression fitted around inner tube 22. Prior to heating shrink tube 36 and forming outer tube 12, mandril 37 is inserted through passageway 21 to further maintain the uniform spacing between the coil turns. As shown, heat shrink tube 36 is somewhat longer than nylon outer tube 12 and has an inside diameter in the range of 0.0825" to 0.0840" with a wall thickness of approximately 0.0015" plus or minus 0.0005". The heat shrink tube is preferably of a fluorinated ethylene propylene heat formable material. The nylon outer tube has a processing temperature range for the heat formation thereof in the range of 356 to 500 degrees Fahrenheit.

FIG. 4 depicts heat shrink tube 36 being oven heated to a temperature of 365 degrees Fahrenheit, which is in the processing temperature range of the nylon outer tube material. As the heat shrink tube shrinks, the heated nylon outer tube material 12 is compressed between coil turns 27–31 in uniform spaces 32–35 to mechanically connect with roughened surface 26 of inner tube 22. The heat formable nylon material tube is also self-leveling, which provides a uniform outer diameter surface for the sheath. Heat shrink tube 36 is then split from the sheath. As previously described, distal end 13 is tapered, and proximal end 15 is flared.

Depicted in FIG. 5 is a partially sectioned view of introducer sheath 40, which represents another aspect of the present invention and an alternative embodiment of introducer sheath 10 of FIG. 2. Introducer sheath 40 includes coaxial inner tube 42, flat wire coil 43, and outer tube 44 with tapered distal end 57 and flared proximal end 58. As previously described, a connector valve 14 is inserted into flared proximal end 58 of the sheath for preventing the backflow of fluids therethrough. The sheath is formed by first winding and compression fitting flat wire coil 43 around inner tube 42 and then heat shrinking and mechanically connecting outer tube 44 to roughened outer surface 46 of the inner tube through the spaces between the coil turns. Radiopaque marker sleeve 72 is positioned distally of the flat wire coil between the inner and outer tubes near the distal end of the sheath. Unlike flat wire coil 23 of sheath 10 in FIG. 2, flat wire coil 43 of FIG. 5 is wound around inner tube 42 to form the compression fit between the inner tube and wire coil. The coil is wound around the inner tube by expanding and wrapping the coil around the inner tube using, for example, a commercially available lathe and a transfer mechanism attached to the carriage of the lathe, which will be described hereinafter. This winding technique improves the manufacturing process and maintains closer tolerances for the uniform spacing between the turns of the coil. In addition, the inner tube is not compressed or collapsed for insertion into the passage of the flat wire coil. This advantageously eliminates any wrinkles in the inner tube wall and maintains closer manufacturing tolerances.

By way of example, kink-resistant, introducer sheath 40 is a 9.6 French (0.126") sheath for inserting a 9.6 French dilator therethrough. Inner tube 42 is a 31 cm length tube of a lubricious material such as polytetrafluoroethylene having a uniform inside diameter in the range of 0.1267" to 0.1282" with a wall thickness of 0.002"±0.001". The inner tube has a minimum inside diameter of 0.126". The lubricious polytetrafluoroethylene material presents a slippery inner surface 45 for easily inserting and withdrawing a dilator as well as other catheters and medical apparatus therethrough. Inner surface 45 is also smooth and nonporous for minimizing the formation of blood clots and other thrombi thereon. Outer surface 46 of the inner tube is chemically etched in a well-known manner for forming a rough outer surface to which outer tube 44 is mechanically connected using the previously described heat shrinking process.

Coil 43 comprises a plurality of flat wire turns, for example, 47–51 with uniform spacing including equal width spaces 52–55 therebetween. Coil 43 is 30 cm in length with an outside diameter of 0.080"±0.005" prior to annealing. The coil is annealed by baking the coil at 800° F. ±25° for approximately ten minutes. After annealing, the outside of the coil has a nominal dimension of 0.085". The coil is formed from 0.004" thick by 0.012" wide flat rectangular stainless steel wire wound with a uniform space in the range of 0.005" to 0.010" between the turns of the coil. Prior to being wound around inner tube 42, wire coil 43 has an inside diameter which is at least 0.040" smaller than the outside diameter of the inner tube. Wire coil 43 is wound and compression fitted around outer surface 46 of inner tube 42 approximately 3–4 mm from the distal end thereof and approximately 5 mm from the proximal end thereof to taper and flare the distal and proximal ends, respectively. After being wound around the outer surface of the inner tube, the spacing between the turns of the coil is approximately 0.007" to 0.009". The coil is wound and compression fitted around inner tube 42 by inserting a mandril having, for example, an outside diameter of 0.1260"+0.0002"−0.0000" through passage 41 of the inner tube and positioning the mandril and tube into the head and tail stock of a commercially available lathe such as the Grizzly Model No. G-1550. A transfer mechanism, as depicted in FIGS. 6–8, is mounted on the carriage of the lathe to wind and compression fit the coil around the inner tube.

Outer tube 44 is 31 cm in length with a preshrunk inside diameter of 0.145"±0.002" and consists of a heat formable polyamide material such as radiopaque nylon that is heat shrunk over coil 43. The outer tube has a nominal preshrunk outside diameter of 0.158". The wall thickness of the nylon tube is approximately 0.0065"±0.001". After the outer tube is heat shrunk and mechanically connected to the inner tube through the turns of the flat wire coil, sheath 40 has a overall nominal wall thickness of 0.011" with an outside diameter of 0.149"±0.002". Tapered distal end 57 of the sheath is formed by grinding externally tapered surface 56 on the distal end of outer tube 44 for a distance of approximately 2 mm from the distal end of radiopaque marker 55. The flared proximal end extends for approximately 5 mm from the proximal end of flat wire coil 43 and is formed using a well-known flaring tool with heat applied to the proximal ends of the tubes.

Prior to heat shrinking the outer tube to the inner tube, radiopaque marker 72 is inserted over the distal end of the inner tube next to flat wire coil 43. Radiopaque marker 72 is approximately 0.050"±0.005" long with an outside diameter of 0.139"±0.0005" and an inside diameter of 0.134"±0.0005". The marker comprises, for example, 10 percent iridium with the remainder being a platinum material.

Figure 6:
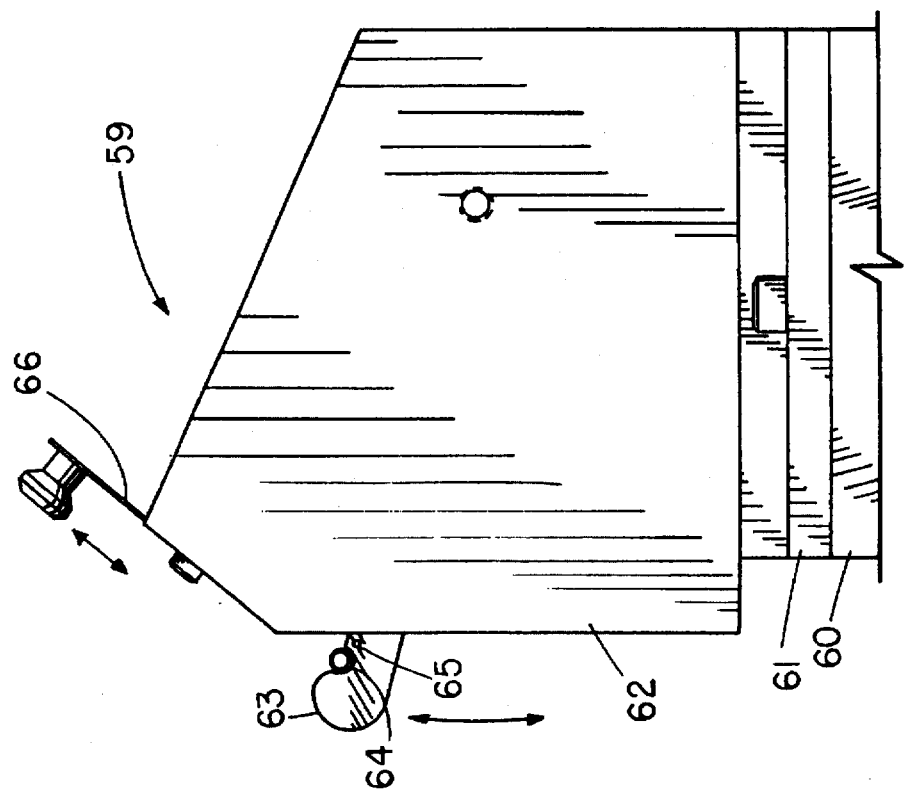
FIG. 6 depicts a side view of a coil transfer mechanism for winding and compression fitting a coil around an inner tube of the sheath of FIG. 5.

Depicted in FIG. 6 is a side view of coil transfer mechanism 59 mounted on carriage 60 of a commercially available lathe such as the previously identified Grizzly Model No. G-1550. This side view is viewed from the tail stock end of the lathe. The coil transfer mechanism includes adapter plate 61, which is horizontally mounted on the carriage of the lathe, and tool holder 62, which is vertically mounted on the horizontal adapter plate. Pivotedly mounted on the tool holder is adjustable guide support 63 with semicircular recess 64 extending through the guide support adjacent the free end thereof. Extending perpendicularly from the guide support toward the tail stock of the lathe is coil retaining pin 65. The coil retaining pin engages the flat wire coil to unwrap the coil while the lathe rotates a mandril with the inner tube mounted thereon. While the mandril and inner tube are being rotated the expanded coil is being wrapped and compression fitted on the outer surface of the inner tube. The transfer mechanism also includes adjustable shield 66 which is positioned adjacent the rotating inner tube to prevent the flat wire coil, which is being unwrapped, from scoring the surface of the inner tube.

Depicted in FIG. 7 is a top view of coil transfer mechanism 59 mounted on lathe carriage 60. Also depicted is head stock 67 and tail stock 68 of the lathe with mandril 69 and inner tube 42 rotatably mounted therebetween. Adjustable guide support 63 has been positioned to cradle mandril 69 and inner tube 42 in recess 64 of the support. Coil retaining pin 65 faces toward tail stock 68 and is adjacent to the rotating mandril and inner tube. The longitudinal axis of the retaining pin and mandril are substantially parallel to one another. Adjustable shield 66 is depicted in a raised position in order to mount the mandril and inner tube between the tail and head stocks. As flat wire coil 43 is wound around inner tube 42, the coil transfer mechanism and the carriage of the lathe move relative to the head and tail stocks as indicated by arrow 70.

FIG. 8 depicts an enlarged view of adjustable guide support 63 and adjustable shield 66 of FIG. 7 with inner tube 42 and mandril 69 positioned therebetween in recess 64 of the support. To start the coil winding process, several turns of coil 43 are manually wrapped around the distal end of inner tube 42 mounted on mandril 69. The next several turns of the wire coil are positioned over coil retaining pin 65, as depicted. Adjustable shield 66 is then slid down and adjacent the inner tube to prevent the remaining free end of the coil from scoring the surface of the rotating inner tube. The lathe is turned on and rotated in the direction of arrow 71 to expand the coil with retaining pin 65 and wrap the coil turns around the outer surface of the rotating inner tube. The coil transfer mechanism moves as indicated by arrow 70 at a speed controlled by the lathe carriage to control the spacing between the coil turns. A uniform spacing between the coil turns of 0.007" to 0.009" is easily maintained using this coil winding procedure. After the desired length of coil is wrapped around the inner tube, the mandril, inner tube and wrapped wire coil are removed from the lathe. The outer radiopaque marker 72 is positioned adjacent the distal end of the coil, and outer tube 55 with a shrink wrap tube positioned thereover is coaxially positioned over the wrapped wire coil and inner tube. The outer tube is then heat shrunk and mechanically connected to the inner tube through the turns of the flat wire coil as previously described with respect to the procedure detailed in FIGS. 3 and 4.

It is to be understood that the above-described flexible, kink-resistant, introducer sheath is merely an illustrative embodiment of the principles of this invention and that other introducer sheaths may be devised by those skilled in the art without departing from the spirit and scope of this invention. It is contemplated that various other materials may be utilized for the inner, outer, and heat shrink tubes. It is also contemplated that introducer sheaths with an inside diameter ranging in size from 5.5 to 14.0 French are readily producible. In summary, the flexible, kink-resistant, introducer sheath provides a thin-wall sheath that is extremely kink-resistant for long-term use applications. The flat wire coil construction of this introducer sheath is also extremely kink-resistant with small outside diameter dilators during introduction through an access site.

What is claimed is:

1. The method of manufacturing a flexible, kink-resistant, introducer sheath comprising the steps of:
    providing an inner tube having an outer diameter and a passageway extending longitudinally therethrough;
    providing a coil having a plurality of turns and an inner diameter less than said outer diameter of said inner tube;
    providing an outer tube;
    winding said coil around said inner tube;
    longitudinally positioning said outer tube around said coil and said inner tube; and
    connecting said outer tube to said inner tube through spaces between said turns.

2. The method of claim 1 wherein the step of connecting said outer tube to said inner tube includes positioning a heat-shrink tube around said outer tube and heating said heat-shrink tube to compress said outer tube through said spaces between said turns.

3. The method of claim 1 wherein the step of winding said coil around said inner tube includes rotating said inner tube, expanding said coil, and wrapping said coil when expanded around said inner tube.

4. The method of manufacturing a flexible, kink-resistant, introducer sheath including an inner tube, a coil, and an outer tube, the inner tube having an outer diameter and a passageway extending longitudinally therethrough, the coil having a plurality of turns and in a relaxed condition an inner diameter less than the outer diameter of the inner tube, comprising the steps of:
    radially expanding the turns of the coil to an inner diameter greater than the outer diameter of the inner tube;
    wrapping the turns of the coil when radially expanded longitudinally around the inner tube;
    connecting the outer tube to the inner tube through spaces between the turns of the coil.

5. The method of claim 4 further comprising inserting a mandril through the passageway of the inner tube and wherein the step of wrapping the turns of the coil includes rotating the inner tube with the mandril inserted therethrough when the turns of the coil are radially expanded.

6. The method of claim 4 further comprising the step of roughening an outer surface of the inner tube and wherein the step of connecting the outer tube to the inner tube includes compressing the outer tube through the spaces between the turns of the coil.

7. The method of claim 6 wherein the step of compressing the outer tube to the inner tube includes positioning a heat-shrink tube around the outer tube and heating the heat-shrink tube.

8. The method of claim 7 further comprising the step of removing the heat-shrink tube from around the outer tube after the outer tube has been compressed through the spaces between the turns of the coil.

9. The method of claim 8 further comprising the step of tapering a distal end of the outer tube after the outer tube has been compressed through the spaces between the turns of the coil.

10. The method of claim 9 wherein the step of tapering a distal end of the outer tube includes grinding the distal end of the outer tube.

11. The method of claim 8 further comprising the step of flaring a proximal end of the inner tube and the outer tube after the outer tube has been compressed through the spaces between the turns of the coil.

12. The method of claim 6 wherein the step of roughening the outer surface of the inner tube includes chemically etching the outer surface of the inner tube.

13. The method of claim 5 further comprising the step of positioning a radiopaque marker at a distal end of the inner tube adjacent to a distal end of the coil after the coil has been wrapped around the inner tube.

14. The method of providing a flexible, kink-resistant, introducer sheath comprising the steps of:

radially expanding a coil having a plurality of turns and in a relaxed condition an inner diameter less than an outer diameter of an inner tube;

wrapping the radially expanded coil longitudinally around the inner tube; and connecting an outer tube to the inner tube through spaces between the turns of the coil wrapped around the inner tube.

15. The method of claim 14 further comprising the step of inserting a mandril through a passageway of the inner tube and wherein the step of wrapping the coil includes rotating the inner tube with the mandril positioned therethrough.

16. The method of claim 14 further comprising the step of longitudinally positioning the outer tube around the inner tube and the coil wrapped longitudinally around the inner tube.

17. The method of claim 16 wherein the step of connecting the outer tube to the inner tube includes compressing the outer tube through the spaces between the turns of the coil.

18. The method of claim 17 wherein the step of compressing the outer tube includes positioning a heat-shrink tube around the outer tube and heating the heat-shrink tube.

19. The method of claim 14 further comprising the step of positioning a radiopaque marker at a distal end of the inner tube adjacent to a distal end of the coil after the coil has been wrapped around the inner tube.

20. The method of claim 14 further comprising the step of tapering a distal end of the outer tube and flaring a proximal end of the inner and the outer tubes.

* * * * *